United States Patent [19]
Bushnell

[11] Patent Number: 5,370,533
[45] Date of Patent: Dec. 6, 1994

[54] DENTAL IMPRESSION TRAY ASSEMBLY AND METHOD OF TAKING IMPRESSIONS

[76] Inventor: Raymond B. Bushnell, 1103 Washington St., Oregon City, Oreg. 97045

[21] Appl. No.: 148,643

[22] Filed: Nov. 8, 1993

[51] Int. Cl.⁵ .............................................. A61C 9/00
[52] U.S. Cl. ........................................ 433/36; 433/37; 433/224
[58] Field of Search ................. 433/36, 37, 41, 42, 433/43, 44, 45, 46, 47, 74, 214

[56] References Cited

U.S. PATENT DOCUMENTS

| | | | |
|---|---|---|---|
| 2,155,334 | 4/1939 | Sitkin et al. | 433/36 |
| 3,211,149 | 10/1965 | Fono | 128/62 A |
| 4,375,965 | 3/1983 | Weissman | 433/37 |
| 4,382,785 | 5/1983 | Lococo | 433/36 |

FOREIGN PATENT DOCUMENTS

| | | | |
|---|---|---|---|
| 2552658 | 4/1985 | France | 433/214 |
| 2602968 | 2/1988 | France | 433/214 |
| 2603185 | 3/1988 | France | 433/214 |

*Primary Examiner*—Cary E. O'Connor
*Attorney, Agent, or Firm*—James D. Givnan, Jr.

[57] ABSTRACT

An impression tray is provided with a dispersal member which receives impression material for delivery into the impression tray. A one-step method includes the provision of barriers on the impression tray to confine light bodied impression material in the tray during the delivery of the material into the tray and the taking of the impression. A two-step method entails the direct deposit of heavy bodied impression material into the impression tray and the taking of a preliminary impression. A jig for punching the preliminary impression confines the impression tray during the formation of passageways for later injected lighter impression material injected into the dispersal member and then to the impression tray. An air cylinder is controlled by an operator for selective discharge of impression material from tubular containers and into the dispersal member. A unitary impression tray is disclosed with a dispersion channel for directing impression material into place.

9 Claims, 2 Drawing Sheets

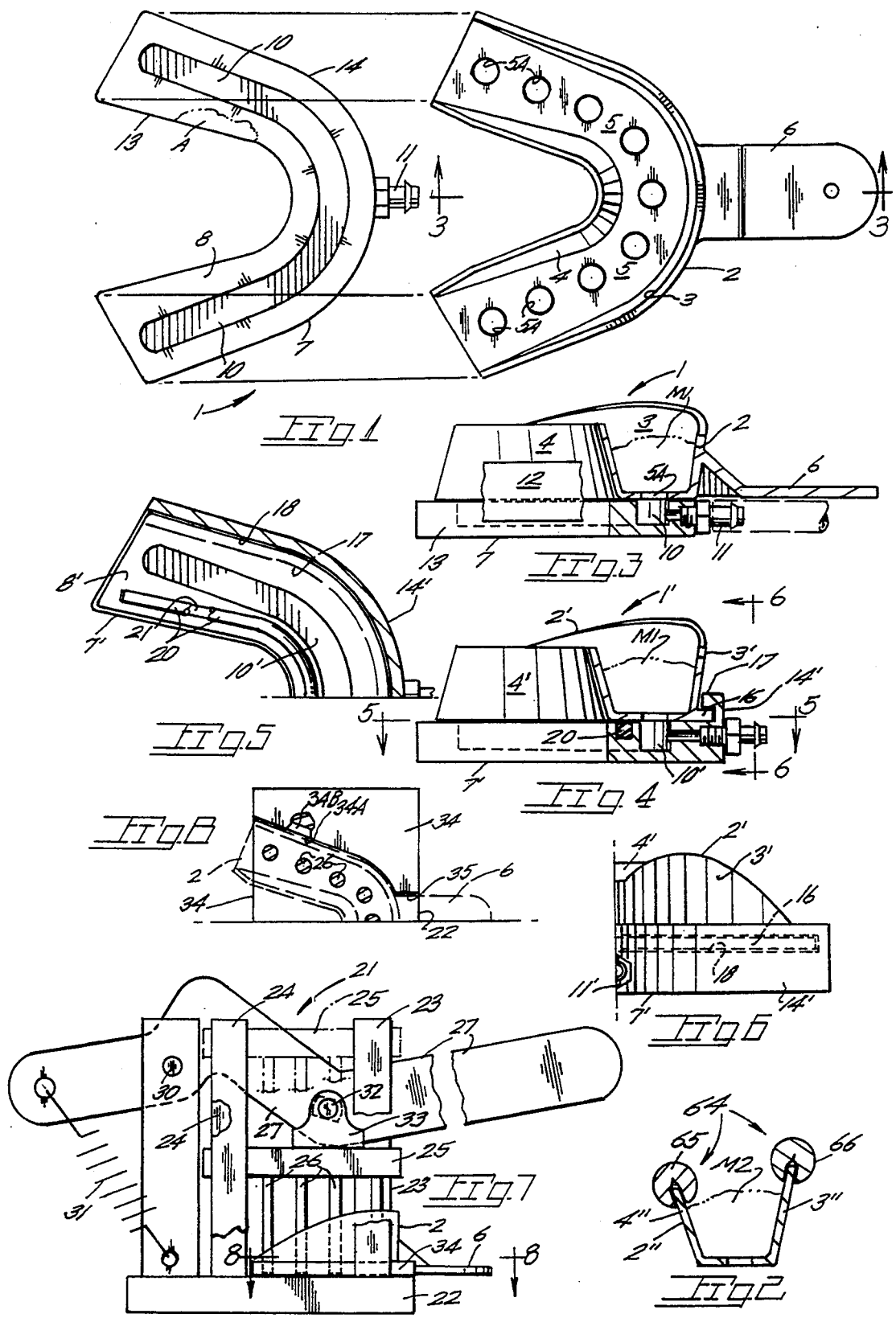

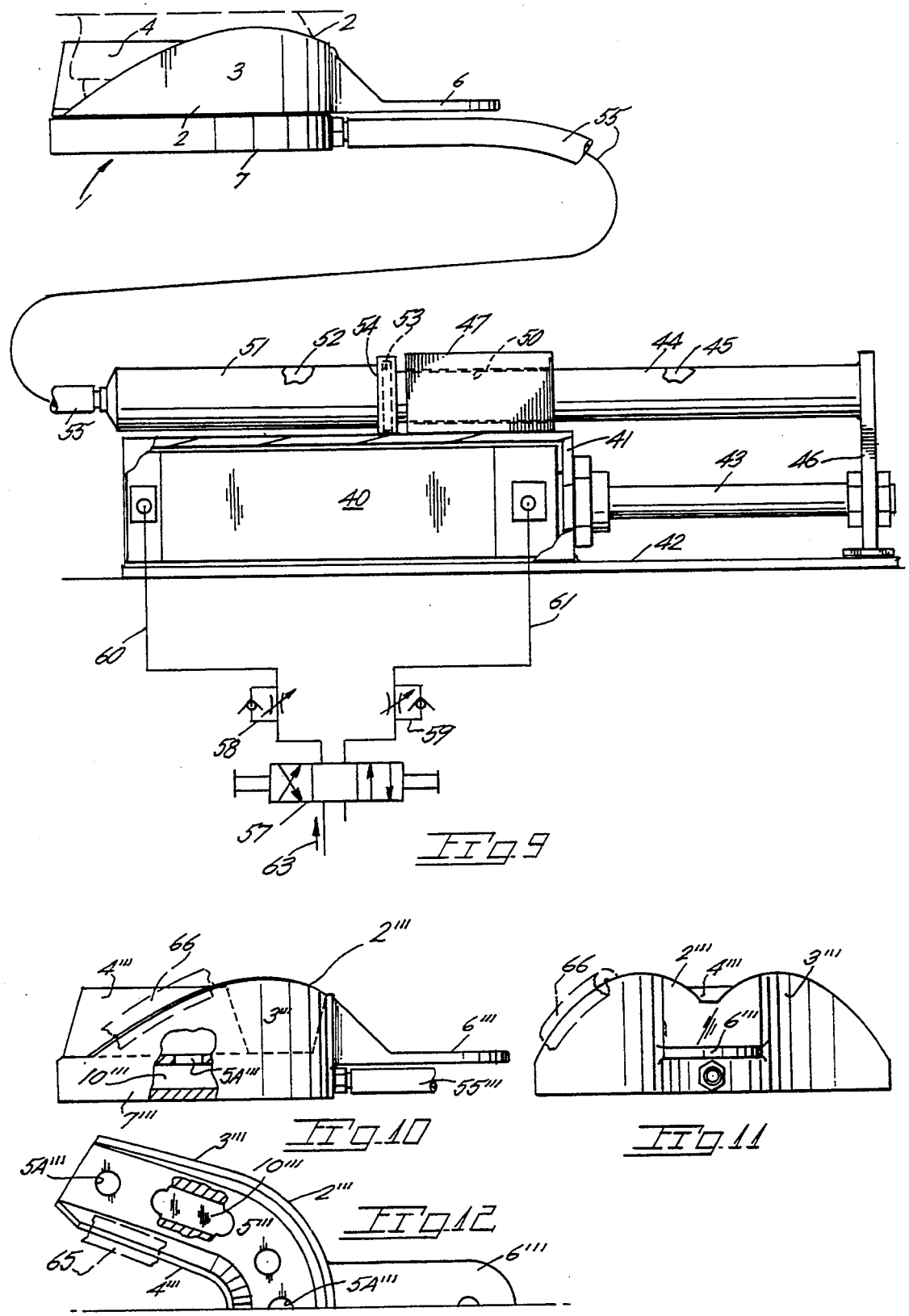

DENTAL IMPRESSION TRAY ASSEMBLY AND METHOD OF TAKING IMPRESSIONS

BACKGROUND OF THE INVENTION

The present invention concerns the making of dental impressions for use in making crowns, caps, bridges, etc.,.

The quality of the above dental items is largely determined by the precise nature of a dental impression taken of the patient's teeth. Impression material is typically deposited into an impression tray whereafter the loaded tray is manually biased upwardly or downwardly for intimate contact with the upper or lower teeth and gums. The impression tray must be carefully applied and removed to avoid subsequent displacement of the impression material and resulting inaccuracy. The displacement procedure currently used hinders the forming of optimum impressions as voids and other inaccuracies caused by saliva, blood and trapped air may occur in the viscous material. The resulting crowns, caps, bridges, etc., hence require considerable corrective effort to re-shape the item or article being constructed. Accordingly, imperfect impressions jeopardize the quality of the finished piece as well as adversely affect their cost by reason of excessive reworking of the finished article.

In wide use in the dental field are impression trays comprising an outer wall and an inner wall which serve to confine impression material deposited in place on a bottom or interconnecting wall of the tray. The tray is provided with an extension for purposes of manipulation of the tray during taking of the impression.

SUMMARY OF THE INVENTION

The present invention is embodied within both structure and method of taking dental impressions wherein the impression material is injected into the tray in place in the patient's mouth. An impression tray is coupled to a dispersal tray which receives impression material from a pressurized source and distributes or injects it at points along the impression tray. In one embodiment of the present invention a preliminary application of heavy bodied impression material is deposited into the impression tray and an initial impression formed which impression is subsequently apertured, to permit the entry of lighter viscosity impression material. In a second embodiment of the invention the impression material is of uniform viscosity and injected into the impression tray via the dispersal tray. In the latter instance the impression tray carries barrier means in place on the tray walls to confine the lighter viscosity material within the tray.

For the charging of the dispersal tray and ultimately the impression tray, a power source is provided, along with a hand held control for regulating the rate at which the impression material is discharged. The impression tray and dispersal tray are coupled in a detachable manner to permit the impression tray and the heavy bodied impression material to be placed in the patient's mouth and subsequently apertured. The impression tray may also be made as one piece for simplicity when using a single step technique.

Important objectives of the present invention include the provision of an impression tray receiving impression material from a dispersal member coupled to the impression tray and through which impression material is injected through a bottom wall of the tray while the latter is in the patient's mouth for a virtually void free impression; the provision of an impression tray provided with dispersal means removably mounted on the tray to permit impression tray use in the usual manner upon completion of taking the dental impressions; the provision of a dispersal tray through which impression material passes from a pressurized source through an apertured cross wall of an impression tray and into intimate contact with the teeth and gums; the provision of a method for utilizing impression material of different viscosities with the lighter viscosity material used to take a precise impression of the patient's teeth while the heavier impression material serves to confine the lighter material; the provision of an impression taking method wherein the discharge of impression material into an impression tray within the patient's mouth is carefully monitored by the user with control means provided the user to regulate the flow of material; the provision of a device for the formation of openings within impression material for the purpose of admitting the passage of impression material of a lighter viscosity into place against the teeth and gums.

BRIEF DESCRIPTION OF THE DRAWINGS

In the drawings:

FIG. 1 is an exploded plan view of a tray assembly of the present invention;

FIG. 2 is a vertical cross sectional view of a modified impression tray;

FIG. 3 is a vertical sectional view taken along line 3—3 of FIG. 1;

FIG. 4 is a view similar to FIG. 3, but showing a modified means of coupling tray assembly components;

FIG. 5 is a horizontal sectional view taken along lines 5—5 of FIG. 4;

FIG. 6 is an end elevational view taken along line 6—6 of FIG. 4;

FIG. 7 is a side elevational view of a punch for the formation of apertures in tray carried impression material;

FIG. 8 is a horizontal sectional view taken along line 8—8 of FIG. 7;

FIG. 9 is a schematic of a tray assembly in communication with pressurized means for loading the tray assembly with impression material;

FIGS. 10, 11 and 12 are side elevational, front elevational and plan views of combined impression tray and dispersal means.

DETAILED DESCRIPTION OF THE PREFERRED EMBODIMENTS

With continuing attention to the drawings wherein reference numerals indicate parts similarly hereinafter identified, the reference numeral 1 indicates generally a tray assembly which receives impression material for the making of a replica of a patient's upper or lower teeth and gums.

Tray assembly 1 includes an impression tray 2 having an outer wall 3 and an inner wall 4 interconnected by a bottom wall 5. Impression trays, in general, are of a size and shape to permit taking an impression of the lower or upper teeth and adjacent gum surfaces. An extension 6 facilitates handling of the tray. Bottom wall 5 is apertured at intervals at 5A. Dispersal means at 7 is adapted for attachment to the unseen or underside of bottom wall 5 by later described means. Dispersal means 7 has a top wall surface 8 with a channel 10 formed therein for communication with the apertures 5A of tray 2. An inlet 11 receives a later described conduit end for the delivery of impression material into channel 10 and ultimately through apertures 5A for progressive contact with the teeth and gums. In a preferred form the wall surface 8 is provided with a suitable tray adhesive at A known to the dental profession permitting attachment to the corresponding shaped under side of wall 5 as shown in FIG. 3, yet which adhesive enables the separation of impression tray 2 from dispersal means 7. An alternative form of coupling tray 2 to dispersal means 7 includes a pressure sensitive adhesive strip 12 having tray adhesive thereon applied along upright walls 3 and 4 of tray 2 and inner and outer surfaces as at 13 and 14 of dispersal means 7. A still further arrangement for joining impression tray 2 to dispersal means 7 is shown in FIGS. 4 and 5 wherein a modified impression tray 2' includes a forwardly projecting lip 16 on outer wall 3'. A modified dispersal means 7' includes a shoulder 17 co-extensive with outer wall 14' and which is grooved at 18 to receive lip 16 to provide interengageable member. To assure snug frictional engagement of lip 16 in groove 18 an elastromeric member 20 is inset within a groove 21 upper surface 8' of the dispersal means to provide an upperwardly biasing force against the underside of impression tray 2' to achieve frictional engagement of lip 16 and shoulder 17. Separation of the dispersal means 7' entails manual compression of the tray assembly and member 20 to release such frictional engagement.

In a preferred method of the present invention, dental tray 2 is charged with first impression material M1 by the direct deposit of the material in the tray. The impression material M1 overlies the apertures 5A of the tray and is confined partially by tray walls 3 and 4. Upon such loading of impression tray 2, an initial impression is taken of the upper or lower teeth with a thin polyethylene film in place on the exposed surface of the impression material. Subsequent to taking of the initial impression the sheet or overlay is removed from the tray and the tray installed within a jig indicated generally at 21 for the formation of openings in the impression material with the openings formed each being in alignment with the apertures 5A of the tray bottom wall. The jig includes a base 22 supporting pairs of guide posts 23 and 24 between which is slidably confined a platform 25 from which depends a series of punches shown as 26. The pins are insertable in the impression material to form a passageway through same for the passage of later injected lighter viscosity impression material. With attention again to jig 21, a lever 27 rocks about a pivot 30 to drive platform 25 downwardly to perforate impression material in place in tray 2. A spring 31 raises the platform and punches 26 to the broken line start position. Lever 27 is coupled to platform 25 in a lost motion manner by a pin 32 in a platform mounted bracket 33 with the pin extending through an elongate opening in handle 27. For positioning of impression tray 2 a tray holder at 34 is mounted in place on base 22 and, as shown in FIG. 8, provided with curved walls as at 34A against which the lower front wall of the impression tray abuts during jig use. The walls 34A terminate at 35 to permit tray extension or handle 6 to project forwardly from base 22. The wall 34A of the tray holder may define a recess 34B for the reception of lip 16 of tray 2'.

With attention now to FIG. 9, a pressurized system for the delivery of impression material to dispersal means 7 and tray 2 is illustrated. A pneumatic cylinder 40, shown as being of the double acting type, is fixed in place within a holder 41 on a platform 42. A piston rod 43 is coupled to a pair of drive tubes 44 and 45, each carried by a carrier plate 46 powered by cylinder 40. A bearing block 47 defines parallel bores as at 50 to guide drive tubes 44 and 45 and align same with tubular containers of impression material at 51 and 52. The containers are equipped with a flange 53 for downwardly inserted placement in a holder 54 having opposed slots for flange reception. A conduit 55 is of a flexible nature to permit injection of the material from the containers 51 and 52 into dispersal means 7 in place in the mouth, while permitting the power source to be at a remote location so as to not interfere with the operator's view of the mouth and tray assembly. A manually operated four way valve at 57 permits the operator to incrementally advance the drive tubes 44 and 45 for expulsion of the impression material in a controlled manner from tubes 51 and 52. A speed control for cylinder 40 is provided by flow control valves 58 and 59 in communication with the cylinder ends via lines 60 and 61. An air pressure source at 63 may be a dental office air system.

A modified form of impression tray is disclosed in FIG. 2 wherein a barrier 64 is provided along the uppermost edges of inner and outer impression tray walls at 3" and 4". The barriers in place atop each of the walls serve to restrict impression material flow in those instances where only a lighter or impression material at M2 is utilized and the earlier described steps of taking an initial impression is dispensed with. Accordingly the admission of lighter viscosity impression material takes place but without the heavier viscosity impression material being in place within tray 2". Accordingly the step of forming openings in the impression material by means of jig 21 is also dispensed with. The wall affixed barriers are formed from pliable material such as lengthwise slotted cotton rolls at 65–66 to cooperate with the patient's inner and outer gum surfaces to confine the lighter impression material. The barrier may also be formed within aerated plastic material suitable for use in the mouth and secured to the tray walls or integral therewith.

The modified impression tray generally at 2''' in FIGS. 9, 10 and 11 include dispersal means at 7''' integral with a tray bottom wall 5'''. Openings 5A''' permit the migration of the lighter bodied dental impression M2 from a channel 10''' upwardly into the impression tray 2''' and into tooth and gum contact. The tray 2''' may be of a disposable nature. Tray 2''' would be used in conjunction with the earlier described method wherein only a single, lighter viscous material is injected into the impression tray. Tray 2''' would be provided with barriers as at 65 and 66, as earlier described, preventing escape of the impression material during the taking of an impression.

While I have shown but a few embodiments of the invention, it will be apparent to those skilled in the art that the invention may be embodied still otherwise without departing from the spirit and scope of the invention.

Having thus described the invention, what is desired to be secured by a Letters Patent is:

I claim:

1. A dental impression tray assembly for temporary placement on a patient's upper or lower teeth and comprising, a tray including inner, outer and bottom walls, one of said walls defining openings, dispersal means having a passageway in communication with said openings, an inlet to receive viscous impression material and to direct the material into said passageway, a conduit serving said inlet, coupling means joining said dispersal means to said tray, a pressurized source of impression material, said pressurized source including a container for the impression material, discharge means including an air cylinder and an operator actuated control means for selectively regulating the operation of said cylinder, a powered member coupled to said cylinder and acting on said container to expel impression material at a desired rate into said conduit.

2. A dental impression tray assembly for placement on a patient's upper or lower teeth and comprising, a tray including inner, outer and bottom walls, one of said walls defining openings, dispersal means having a passageway in communication with said openings, an inlet to receive viscous impression material and to direct the material into the passageway, coupling means joining said dispersal means to said tray, and said dispersal means includes a U-shaped member having a planar wall surface, said coupling means being an adhesive layer joining said wall surface to said tray.

3. The impression tray assembly claimed in claim 2 wherein said coupling means includes a pressure sensitive adhesive strip.

4. A dental impression tray assembly for placement on a patient's upper or lower teeth and comprising, a tray including inner, outer and bottom walls, one of said walls defining openings, dispersal means having a passageway in communication with said openings, an inlet to receive viscous impression material and to direct the material into the passageway, coupling means joining the dispersal means to the tray, said coupling means includes interengageable members on said tray and said dispersal means, an elastomeric member biasing the interengageable members into frictional engagement.

5. The method of making a dental impression including the steps of:

depositing impression material in an impression tray, applying the tray and the impression material to the patient's teeth and gum surface for an initial impression, installing the tray in a jig for the formation of passageways in the impression material, placing the impression tray on some of a patient's teeth, actuating a control for pressurizing an air cylinder for the discharge of additional impression material from a container, and directing the flow of said additional impression material to dispersal means in communication with the interior of said impression tray and through said passageways and into contact with the patient's teeth and gums.

6. The method claimed in claim 5 additionally including the step of positioning a film of pliable sheet material over the first mentioned deposited impression material prior to taking the initial impression.

7. The method claimed in claim 5 including the step of providing barriers on the impression tray to confine impression material in said tray.

8. A dental impression tray assembly comprising, a tray for receiving impression material including inner, outer and bottom walls with the bottom wall defining openings, and dispersal means integral with the bottom wall and defining a channel along which dental impression material may flow, said channel closed at its ends to define a chamber in communication with said openings, an inlet serving said channel and for receiving pressurized impression material from a conduit for delivery to the tray bottom wall via said openings, said dispersal means includes a pressurized source of impression material, said source including a container for impression material, discharge means including an air cylinder, operator actuated control means for selectively regulating the operation of said cylinder, a powered member coupled to said cylinder and acting on said container to expel impression material into said conduit at a desired rate.

9. The impression tray claimed in claim 8 additionally including barriers in place on said walls to confine the impression material within said tray.

* * * * *